(12) United States Patent
Nielsen et al.

(10) Patent No.: US 8,204,579 B2
(45) Date of Patent: Jun. 19, 2012

(54) DEVICE AND METHOD FOR DETERMINING A CONCENTRATION-RELATED QUANTITY OF A FLUORESCENT CONTRAST AGENT APPLIED TO A TURBID MEDIUM

(75) Inventors: Tim Nielsen, Hamburg (DE); Thomas Koehler, Norderstedt (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 722 days.

(21) Appl. No.: 12/307,777

(22) PCT Filed: Jun. 25, 2007

(86) PCT No.: PCT/IB2007/052450
§ 371 (c)(1),
(2), (4) Date: Jan. 7, 2009

(87) PCT Pub. No.: WO2008/007271
PCT Pub. Date: Jan. 17, 2008

(65) Prior Publication Data
US 2009/0326382 A1    Dec. 31, 2009

(30) Foreign Application Priority Data

Jul. 7, 2006    (EP) .................................... 06116764

(51) Int. Cl.
*A61B 6/00*    (2006.01)
*A61B 5/00*    (2006.01)
(52) U.S. Cl. ........ 600/477; 600/476; 600/473; 600/431; 600/317; 600/310
(58) Field of Classification Search .................. 600/475, 600/477, 473, 476, 431, 310, 317; 250/302
See application file for complete search history.

(56) References Cited

U.S. PATENT DOCUMENTS
5,952,664 A    9/1999    Wake et al.
(Continued)

FOREIGN PATENT DOCUMENTS
WO    0195795 A2    12/2001

OTHER PUBLICATIONS

Yoo K M, et al; "Imaging Objects Hidden in Scattering Media Using a Fluorescence—Absorption Technique" Optics Letters, OSA, Optical Society of America, Washington, DC, US, vol. 16, No. 16, Aug. 15, 1991 pp. 1252-1254, XP000220055 ISSN: 0146-9592.
Braunstein, Matthew et al: DYE-Enhanced Multispectral Transillumination for Breast Cancer Detection: Feasibility Measurements, Proceedings—19th International Conference—IEEE/EMBS Oct. 30-Nov. 2, 1997 Chicago, IL. USA, pp. 685-688.

*Primary Examiner* — Long V. Le
*Assistant Examiner* — Helene Bor

(57) ABSTRACT

A device for determining a concentration-related quantity of a fluorescent contrast agent applied to an object (2), in particular a turbid medium. Said device generally comprises a source (4) of electromagnetic radiation for irradiating the object (2) at an excitation wavelength and at least one first detecting means (6, 7.1, 7.2, . . . , 8) for detecting fluorescent electromagnetic radiation emitted by the contrast agent at a fluorescence wavelength, said first detecting means producing fluorescence intensity data (F). The proposed device further comprises at least one second detecting means (6, 7.1, 7.2, . . . ) for detecting electromagnetic radiation transmitted by the object (2) at the excitation wavelength, said second detecting means producing transmission intensity data (T), and evaluating means (10) adapted to receive the transmission intensity data and the fluorescence intensity data and to determine said concentration-related quantity of the contrast agent from a ratio (R) of fluorescence intensity data and transmission intensity data.

18 Claims, 4 Drawing Sheets

U.S. PATENT DOCUMENTS

| | | | |
|---|---|---|---|
| 6,175,759 B1 * | 1/2001 | Chan et al. | 600/431 |
| 6,219,566 B1 | 4/2001 | Weersink et al. | |
| 6,280,386 B1 * | 8/2001 | Alfano et al. | 600/431 |
| 6,397,099 B1 * | 5/2002 | Chance | 600/473 |
| 6,415,172 B1 * | 7/2002 | Painchaud et al. | 600/407 |
| 6,615,063 B1 | 9/2003 | Ntziachristos et al. | |
| 2002/0045833 A1 | 4/2002 | Wake et al. | |
| 2002/0111550 A1 * | 8/2002 | Schwamm et al. | 600/419 |

* cited by examiner

DEVICE AND METHOD FOR DETERMINING A CONCENTRATION-RELATED QUANTITY OF A FLUORESCENT CONTRAST AGENT APPLIED TO A TURBID MEDIUM

BACKGROUND OF THE INVENTION

The present invention relates to a device for determining a concentration-related quantity of a fluorescent contrast agent applied to an object, in particular a turbid medium, said device comprising a source of electromagnetic radiation for irradiating the object at an excitation wavelength and at least one first detecting means for detecting fluorescent electromagnetic radiation emitted by the contrast agent at a fluorescence wavelength, said first detecting means producing fluorescence intensity data.

The present invention also relates to a method of determining a concentration-related quantity of a fluorescent contrast agent applied to an object, in particular a turbid medium, said method comprising irradiating the object with electromagnetic radiation at an excitation wavelength and detecting fluorescent electromagnetic radiation emitted by the contrast agent at a fluorescence wavelength, thereby producing fluorescence intensity data.

The present invention further relates to a computer program product for determining a concentration-related quantity of a fluorescent contrast agent applied to an object, in particular a turbid medium, and to an optical imaging system for imaging an object, in particular a turbid medium, by monitoring fluorescent radiation emitted by a fluorescent contrast agent applied to the object.

Optical imaging systems for imaging a turbid medium, in particular optical mammography systems for imaging female breast tissue, generally employ a fluorescent contrast agent which is applied to an object to be imaged, e.g. a female breast. Electromagnetic radiation that is incident on the object penetrates into the object and excites the fluorescent contrast agent comprised therein which in turn produces fluorescent radiation (in the near infrared (NIR) range of the optical spectrum). The fluorescent radiation emerging from the object is detected at several orientations or locations relative to the object.

Generally, the contrast agent will not be distributed evenly within an object to be imaged. For instance, in optical fluorescence mammography the agents are taken up in higher concentrations by a tumour than by surrounding healthy tissue, i.e. the relative contrast between lesion (tumour) and background is established by the physiology of the contrast agent uptake. An absolute concentration of the contrast agent can be varied by changing the dose that is injected into the object (administered to a patient) or by varying the time after injection at which imaging is performed.

The minimum concentration of contrast agent useful for acquiring images is given by the detection sensitivity of the imaging system. However, there exists an upper limit of the concentration which is given by the onset of non-linear behaviour of the fluorescence signal due to self-absorption of radiation by the contrast agent. These non-linearities have to be avoided when performing optical imaging because they have an important impact on the observed contrast between those parts of the object which take up lower concentrations of contrast agents, e.g. healthy tissue, and those object regions which take up higher concentrations of contrast agents, e.g. lesions: in the low concentration regime a lesion appears as a bright spot on a relatively dark background. In the high-concentration regime a lesion appears as a relatively dark spot.

OBJECT OF THE INVENTION

It is the object of the present invention to provide an optical imaging system for imaging objects by using fluorescent contrast agents and a corresponding method which enable determining an optimum dose of applied contrast agent and/or an optimum time for performing imaging of the object, wherein said optimum dose is high enough to be detected but not too high in order to avoid non-linearities. It is also an object of the present invention to provide a device and a computer program product for use in an optical imaging system which translates said method into practice.

SUMMARY OF THE INVENTION

According to a first aspect of the present invention the object is achieved by providing a device of the above-defined type having at least one second detecting means for detecting electromagnetic radiation transmitted by the object at the excitation wavelength, said second detecting means producing transmission intensity data, said device further comprising evaluating means adapted to receive the transmission intensity data and the fluorescence intensity data and to determine said concentration-related quantity of the contrast agent from a ratio of fluorescence intensity data and transmission intensity data.

According to a second aspect of the present invention, the object is achieved by providing an optical imaging system of the above-defined type, which comprises a device according to said first aspect of the present invention, wherein operation of the system is controlled in accordance with the concentration-related quantity determined by said device.

According to a third aspect of the present invention the object is achieved by providing a computer program product of the above-defined type, comprising first code sequences for receiving fluorescence intensity data descriptive of fluorescent electromagnetic radiation emitted by the object; second code sequences for receiving transmission intensity data descriptive of electromagnetic radiation transmitted by the object; third code sequences for calculating a ratio of the fluorescence intensity data and the transmission intensity data and for determining said concentration-related quantity from said ratio.

According to a fourth aspect of the present invention the object is achieved by providing a method of the above-defined type, said method further comprising detecting electromagnetic radiation transmitted by the object at the excitation wavelength, thereby producing transmission intensity data; calculating a ratio of the fluorescence intensity data and the transmission intensity data; and determining said concentration-related quantity of the contrast agent from said ratio.

Thus, in accordance with a general idea underlying the present invention a simple approach is proposed that allows to verify whether or not an average contrast agent concentration in the object is suited for optical imaging purposes. The approach makes use of a fluorescence measurement and a transmission measurement that can be applied directly to raw data or signals generated by said measurements: a ratio of the fluorescence signal with respect to the transmission signal is determined as a function of distance between source and detector. If the contrast agent concentration is in a range where self-absorption can be neglected, the data corresponding to said ratio will show a different behaviour than in the case where the contrast agent concentration is too high. Therefore, by analysing the behaviour of said fluorescence-transmission ratio the average contrast agent concentration in the object, e.g. a female breast, can be determined in a quantitative way. Hereinafter, this will be referred to as a concentration-related quantity (too high; appropriate).

In one embodiment of the method in accordance with the present invention a distance between said first detecting means and said radiation source and said second detecting means and said radiation source is variable for producing distance-dependent fluorescence intensity data and transmission intensity data. In this way, said ratio can be analysed as a function of source detector distance, for instance by optical inspection of a corresponding plot or by performing a regression on the corresponding data. For instance, if the contrast agent concentration is in a range where self-absorption can be neglected, the ratio data will lie on a line, i.e. shows linear behaviour with source detector distance. Furthermore, the slope of this line is proportional to the contrast agent concentration. It is therefore possible to derive absolute concentration values if the system is suitably calibrated. On the other hand, if the concentration is too high the ratio data will lie on an essentially S-shaped curve.

In a corresponding embodiment of the method in accordance with the present invention the latter comprises varying a distance between a radiation source and a detecting position for producing distance-dependent transmission intensity data and fluorescence intensity data and determining said concentration-related quantity from a behavior of said ratio as a function of said distance.

In a further embodiment of the device in accordance with the present invention, the latter comprises a plurality of first and second detecting means located at respective distances from the radiation source for detecting fluorescent electromagnetic radiation and transmitted electromagnetic radiation at various positions relative to the object.

In this way, distance-dependent fluorescence and transmission data can be generated by collecting data from different first and/or second detecting means.

In order to capture fluorescent radiation from the object, the at least one second detecting means is sensitive in the near infrared range of the optical spectrum.

As already indicated above, in a further embodiment of the device in accordance with the present invention the evaluating means is adapted to determine an amount of self-absorption of radiation by the contrast agent from a behaviour of said ratio with said distance in order to determine concentration regimes suitable for optical imaging.

For to determine said concentration-related quantity by visual inspection, in yet another embodiment of the device in accordance with the present invention the latter comprises display means for displaying a curve of said ratio plotted as a function of said distance.

If a plurality of detecting means is used for analysing an object, said object—due to its geometry—may not be in suitable operative connection with all of said detecting means. Therefore, in another embodiment of the device in accordance with the present invention the latter comprises means for accounting for a position of the object relative to said plurality of first and second detecting means for to determine which fluorescence intensity data and which transmission intensity data are to be included in said ratio depending on said relative position.

In a further embodiment of the device in accordance with the present invention the evaluating means is adapted to notify a first type of concentration-related quantity of the contrast agent if said ratio varies linearly with the distance and a second type of concentration-related quantity of the contrast agent is said ratio varies non-linearly with the distance. In this way, the evaluating means can be used to automatically control operation of an optical imaging system.

When monitoring of contrast agent kinetics is required, in yet another embodiment of the device in accordance with the present invention the at least one first and second detecting means are adapted to continuously produce said intensity data over a predetermined time interval.

In a corresponding embodiment of the method in accordance with the present invention the latter comprises determining said concentration-related quantity continuously over a predetermined time interval.

At least said radiation source and said first and second detecting means can be comprised in a hand-held unit thus constituting a simple hand-held device for to determine contrast agent or dye concentration.

In order to facilitate practical use of the device in accordance with the present invention, in a further embodiment the latter further comprises a hollow unit for surrounding the object to be imaged. Said hollow unit comprises a plurality of first optical fibres in connection with said radiation source for irradiating the object inside the hollow unit. Furthermore, the hollow unit comprises a plurality of second optical fibres in connection with a common detector unit for detecting radiation from the object inside the hollow unit. A switchable wavelength-selective filter means is provided in connection with said second optical fibres and/or said detector unit for selectively providing said first and second detecting means, respectively.

In order to achieve uniform radiation and detection of objects of various shapes and sizes, in yet another embodiment of the device in accordance with the present invention, said first and second optical fibres are distributed in essentially uniform fashion on a surface of said hollow unit.

In this context, in another embodiment of the device in accordance with the present invention, generating distance-dependent transmission and fluorescence data can be achieved by providing a multiplexing means for selectively irradiating the object through one of said first optical fibres, which effectively functions as a radiation source and is located at a given distance from respective ones of said second optical fibres.

In a further embodiment of the method in accordance with the present invention the latter comprises outputting a control signal depending on a measure of said concentration-related quantity. Said control signal can then be used for controlling the optical imaging system in accordance with said aspect of the present invention.

Further advantages and characteristics of the present invention can be gathered from the following description of preferred embodiments given by way of example only with reference to the enclosed drawings. Features mentioned above as well as below can be used in accordance with the present invention either individually or in conjunction. The described embodiments do not form an exhaustive enumeration but should be regarded as examples in connection with a general concept underlying the present invention.

DETAILED DESCRIPTION

Figure 1:
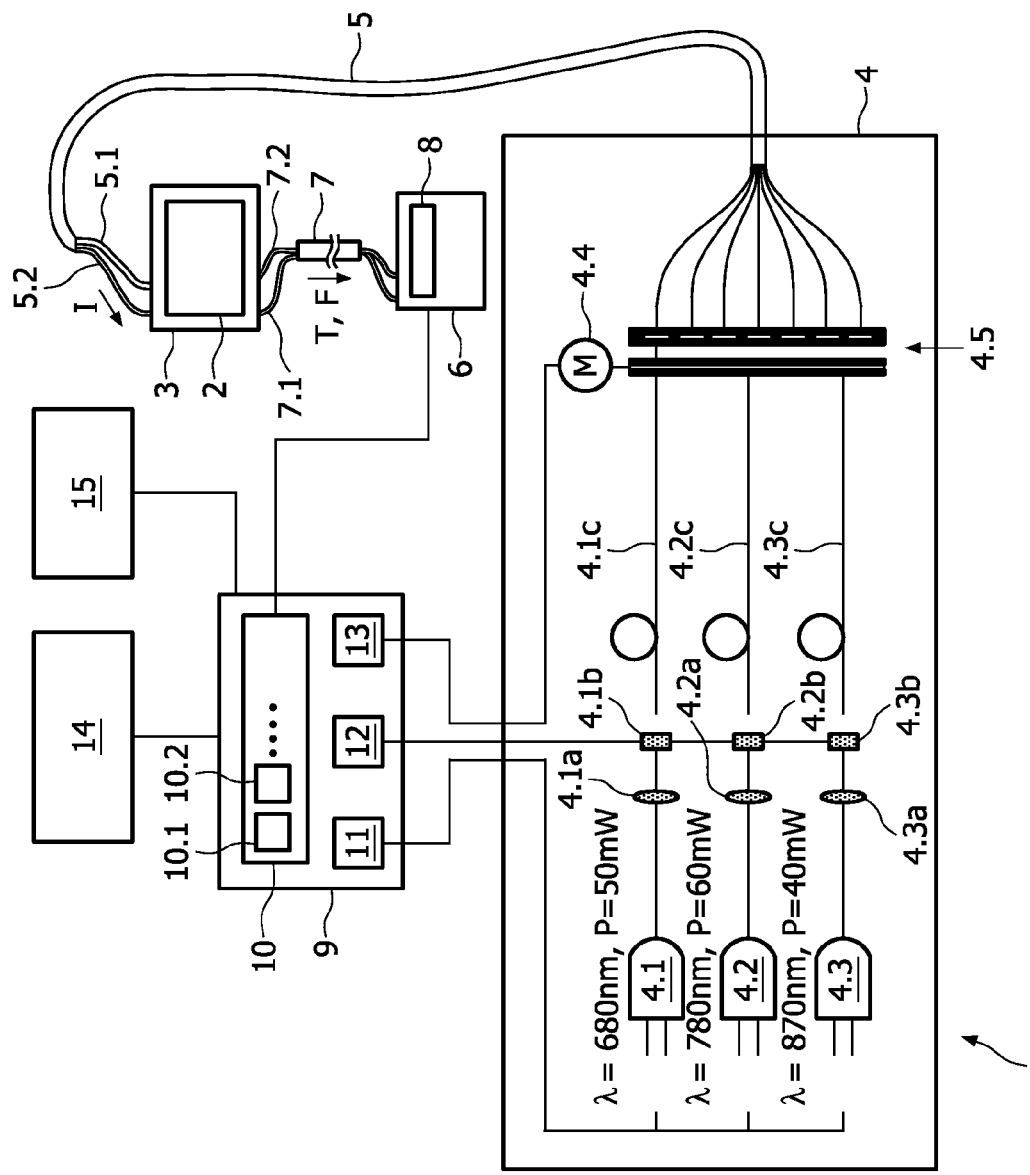
FIG. 1 is a schematic block diagram of an optical imaging system comprising a device for determining a concentration-related quantity of a fluorescent contrast agent applied to an object in accordance with the present invention.

FIG. 1 shows a schematic block diagram of an optical imaging system 1 comprising a device for determining a concentration-related quantity of a fluorescent contrast agent applied to an object in accordance with the present invention. Optical imaging system 1 is devised for imaging an object 2, in particular a turbid medium, e.g. human or animal tissue, such as female breast tissue, by monitoring fluorescent radiation emitted by a fluorescence contrast agent (not shown) applied to the object 2. The latter generally is comprised inside a hollow object-surrounding unit 3 which is connected to a radiation source 4 via radiation guiding means 5. Hollow unit 3 is further connected to a detector unit 6 via further radiation guiding means 7. Both radiation guiding means 5 and further radiation guiding means 7 comprise a plurality of radiation guiding fibres, preferably 256 fibres of diameter d=1 mm each, only some of which 5.1, 5.2, . . . ; 7.1, 7.2, . . . are depicted for reason of clarity.

Detector unit 6 comprises a plurality of detectors (not shown), a number of which corresponds to the number of fibres in radiation guiding means 7, each of said detectors being connected with one of said fibres for detecting radiation transmitted thereon. Detector unit 6 further comprises a filter means 8.

Detector unit 6 is connected with a control unit 9 of the optical imaging system 1, preferably devised in the form of a Personal Computer (PC). Control unit 9 comprises an evaluating means 10, a laser controller 11, a shutter controller 12, and a motor controller 13, the functioning of which will become apparent later. Evaluating means 10, laser controller 11, shutter controller 12, and motor controller 13 are preferably devised in software form and may be implemented on control unit 9 by means of any suitable programming language, e.g. C, C++, Java, or the like, as known to a person skilled in the art.

Evaluating means 10 further includes a number of modules 10.1, 10.2, . . . , preferably also devised in software form, the functioning of which will also become apparent later.

Furthermore, the optical imaging system 1 comprises display means 14 and input means 15 connected with said control unit 9.

According to the embodiment of FIG. 1, radiation source 4 further comprises a number of laser diodes 4.1, 4.2, 4.3 in operative connection with a respective lens 4.1a, 4.2a, 4.3a and shutter 4.1b, 4.2b, 4.3b followed by a respective length of radiation guiding fibre 4.1c, 4.2c, 4.3c, preferably of diameter d=0.4 mm. In the embodiment shown, the first laser diode 4.1 emits electromagnetic radiation at a first excitation wavelength and with a first emission power, e.g. $\lambda$=680 nm, P=50 mW. The second laser diode 4.2 emits electromagnetic radiation at a second excitation wavelength and with a second emission power, e.g. $\lambda$=780 nm, P=60 mW. The third laser diode 4.3 emits $\lambda$=780 nm, P=60 mW electromagnetic radiation at a third excitation wavelength and with a third emission power, e.g. $\lambda$=870 nm, P=40 mW.

Radiation source 4 further comprises motor means 4.4 in operative connection with a multiplexing means 4.5 in the form of a fibre selector adapted to select one of said plurality of radiation guiding fibres 5.1, 5.2, . . . of the first radiation guiding means 5.

Operation of the optical imaging system 1 will be described in the following:

In a general way, object 2 with applied fluorescence contrast agent is irradiated with electromagnetic radiation from radiation source 4 via radiation guiding means 5, i.e. radiation guiding fibres 5.1, 5.2, . . . , as indicated by means of arrow I in FIG. 1, at least one an excitation wavelength. Contrast agent in object 2 then absorbs part of said radiation and emits fluorescent radiation at a wavelength different from said excitation wavelength which is detected by means of detector unit 6, i.e. the individual detectors comprised therein, via radiation guiding means 7, i.e. radiation guiding fibres 7.1, 7.2, . . . . Selectively detecting said fluorescent radiation only is achieved by employing filter means 8 which is devised for efficiently blocking said excitation wavelength. In FIG. 1, said fluorescent radiation from object 2 is depicted by means of arrow F. Hereinafter, reference sign F will also be used to denote corresponding data, i.e. fluorescence intensity data, produced by detector unit 6 in response to said fluorescence radiation.

Since different structures in object 2 will include different concentrations of the fluorescence contrast agent, spatially resolved detection of said fluorescent radiation enables to resolve structural features of object 2. Said structural resolution can be achieved by suitably positioning radiation guiding fibres 7.1, 7.2, . . . on a surface of hollow unit 3 (cf. appended FIG. 2) comprising object 2, as known to a person skilled in the art.

Corresponding fluorescence intensity data is then provided from detector unit 6 to control unit 9 for displaying on a display means 14, e.g. a monitor or printer.

Figure 2:
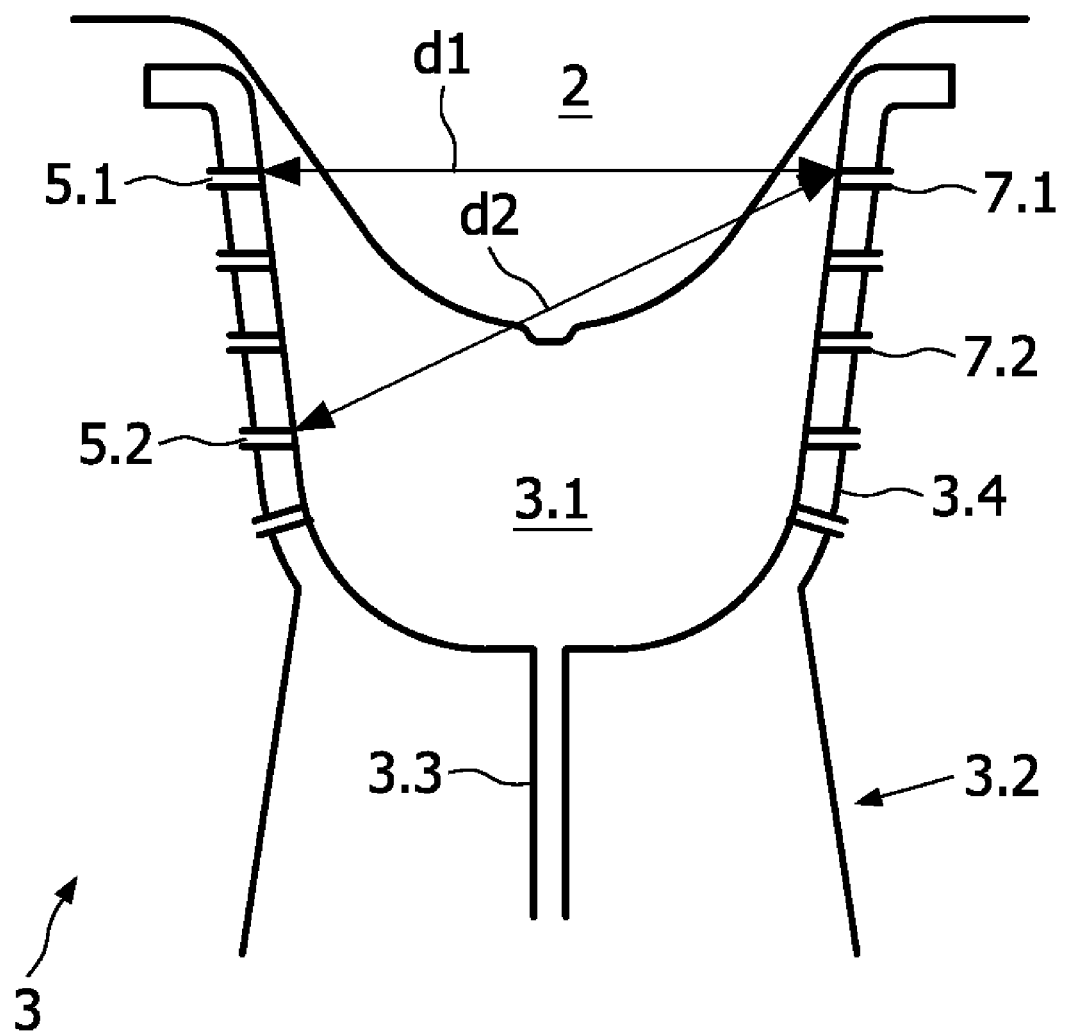
FIG. 2 is a schematic diagram of an object-surrounding unit in the device of FIG. 1.

In accordance with physical characteristics of the object 2 and/or the fluorescence contrast agent used, laser controller 11 may command emission of radiation by one or more of said laser diodes 4.1-4.3. Accordingly, shutters 4.1b, 4.2b, 4.3b are controlled by means of shutter controller 12 for guiding said emitted radiation via respective fibre 4.1c, 4.2c, 4.3c to fibre selector 4.5. The at least one selected excitation wavelength is then in turn provided to each of said radiation guiding fibres 5.1, 5.2, . . . in radiation guiding means 5 for irradiating object 2 in a spatially resolved fashion. To this end, as indicated in FIG. 1, the individual radiation guiding fibres 5.1, 5.2, . . . of radiation guiding means 5 are suitably distributed over a surface of said hollow unit 3 (cfc. FIG. 2), comprising the object 2, as known to a person skilled in the art.

In this way, according to an embodiment of the present invention only one of said radiation guiding fibres 5.1, 5.2, . . . is active for irradiating object 2 at a time, whereas all of said radiation guiding fibres 7.1, 7.2, . . . are simultaneously active for capturing radiation from object 2 and for guiding said captured radiation to detector unit 6, thus effectively constituting a plurality of detecting means for detecting said fluorescent radiation.

In order to determine at least one concentration-related quantity of the fluorescence contrast agent inside object 2, further to said fluorescent radiation F the system of FIG. 1 is devised for measuring a transmission radiation by said object 2. This is indicated by means of arrow T in FIG. 1. Note that reference sign T will also be used to designate corresponding data generated by detector unit 6. In other words: beside said fluorescent radiation F detector unit 6 also detects a component T of said radiation I which is transmitted by object 2 without any interaction with the fluorescence contrast agent.

To this end, filter means 8 is not employed within detector unit 6, and corresponding transmission intensity data T is provided to control unit 9.

Again, owing to the design of hollow unit 3, radiation guiding fibres 7.1, 7.2, . . . and detector unit 6, effectively a plurality of detecting means is provided for detecting said transmission radiation.

As can best be seen from FIG. 2, the above-described multiplexing of radiation guiding fibres 5.1, 5.2, . . . by means of fibre selector 4.5 in connection with spatially resolved detection by means of radiation guiding fibres 7.1, 7.2, . . . is equivalent to varying a source detector distance within the optical imaging system 1 of FIG. 1.

FIG. 2 shows a schematic diagram of a hollow object-surrounding unit 3 in the device of FIG. 1. Hollow unit 3 is devised in the form of a cup, an interior 3.1 of which is at least partly filled with a radiation transmitting fluid, as known to a person skilled in the art. The other part of the interior 3.1 of said cup comprises the object 2. In the embodiment of FIG. 2, hollow unit 3 is particularly designed for holding a female breast in the context of mammographical imaging.

In its bottom region 3.2, said cup comprises a channel 3.3 for inflow and outflow of said fluid. Radiation guiding fibres 5.1, 5.2, . . . ; 7.1, 7.2, . . . (cf. FIG. 1) terminate in corresponding openings in a side wall 3.4 of said cup such that electromagnetic radiation guided by fibres 5.1, 5.2, . . . may enter the interior 3.1 of said cup and may subsequently be captured by radiation guiding fibres 7.1, 7.2, . . . for guiding to detector unit 6 (FIG. 1).

As stated before, multiplexing of said radiation guiding means 5.1, 5.2, . . . effectively corresponds to varying a source detector distance, as illustrated in FIG. 2: while a termination of radiation guiding fibre 5.1 is located at a distance d1 from a termination of radiation guiding fibre 7.1, a termination of radiation guiding fibre 5.2 is located at a longer distance d2, d2>d1, from said termination of radiation guiding fibre 7.1. Thus, by irradiating the interior 3.1 of said cup, i.e. object 2, first by means of radiation guiding fibre 5.1 and subsequently by means of radiation guiding fibre 5.2, a transmission intensity and/or fluorescence intensity detected by means of radiation guiding fibres 7.1 effectively provides measurement data from two different source detector distances, i.e. distances d1 and d2, respectively. By multiplexing over said plurality of radiation guiding fibres 5.1, 5.2, . . . (FIG. 1) distance-dependent measurement data from a broad range of source detector distances, generally denoted SD or dij, can be gathered.

Source detector distances dij; i, j=1, 2, . . . , n, where n is the number of individual radiation guiding fibres used in radiation guiding means 5, 7, i.e. n=256 in the present example, are known from system geometry, i.e. spatial distribution of said radiation guiding fibres 5.1, 5.2, . . . ; 7.1, 7.2, . . . on the surface or side wall 3.4 of hollow unit 3. In other words, for a given activated irradiating fibre 5.1, 5.2, . . . all of the source detector distances, i.e. distances of detecting fibres 7.1, 7.2, . . . to said activated fibre are known from system geometry and may be stored in and provided by suitable storage means (not shown) of control unit 9 (FIG. 1). In other words: for a given irradiating fibre each detector in detector unit 6 provides data with respect to a known source detector distance SD.

As already stated above, for a given activated irradiating fibre 5.1, 5.2, . . . both distance-dependent transmission intensity data T and fluorescence intensity data F can be determined by detector unit 6 by way of selectively employing filter means 8. Both distance-dependent transmission intensity data and fluorescence intensity data are then transmitted to evaluating means 10 of control unit 9 for further analysis.

As shown in exemplary fashion in above-described FIG. 1, evaluating means 10 comprises a number of (software) modules 10.1, 10.2, . . . . By means of one of said modules, e.g. module 10.1, evaluating means 10 is adapted to receive the distance-dependent transmission intensity data T and the distance-dependent fluorescence intensity data from detector unit 6. By means of another one of said modules, e.g. module 10.2, evaluating means 10 is further adapted to calculate a ratio of said distance-dependent transmission intensity data and said distance-dependent fluorescence intensity data. If R denotes said ratio, F denotes said distance-dependent fluorescence intensity data, and T denotes said distance-dependent transmission intensity data, then said ratio R is defined as R=F/T. Note that in accordance with the dependence of both the fluorescence intensity data and the transmission intensity data on the above-defined source detector distance, said ratio R also is dependent on said source detector distance.

Another one of said modules 10.1, 10.2, . . . of evaluating means 10 may be adapted to account for a position of the object 2 relative to said plurality of first and second detecting means for to determine which fluorescence intensity data F and which transmission intensity data T are to be included in said ratio R depending on said relative position.

Yet another one of said modules 10.1, 10.2, . . . of evaluating means 10 may be adapted to display a plot of said ratio R as a function of the source detector distance on display means 14 (FIG. 1).

Note that according to the embodiments of FIGS. 1 and 2, transmission T and fluorescence F are measured using common radiation guiding fibres 7.1, 7.2, . . . , such that for determining said ratio R for a given source detector distance, i.e. a given radiation guiding fibre 7.1, 7.2, . . . , a simple division operation involving respective measured values on said fibre is required. This has advantages with respect to calibration. However, in another embodiment in accordance with the present invention different radiation guiding fibres may be used for measuring transmission T and fluorescence F, respectively. For determining said ratio R, corresponding signals from a first group of radiation guiding fibres, e.g. used for measuring transmission T, then have to be interpolated to the locations of a second group of radiation guiding fibres, e.g. used for measuring transmission T.

Figure 3:
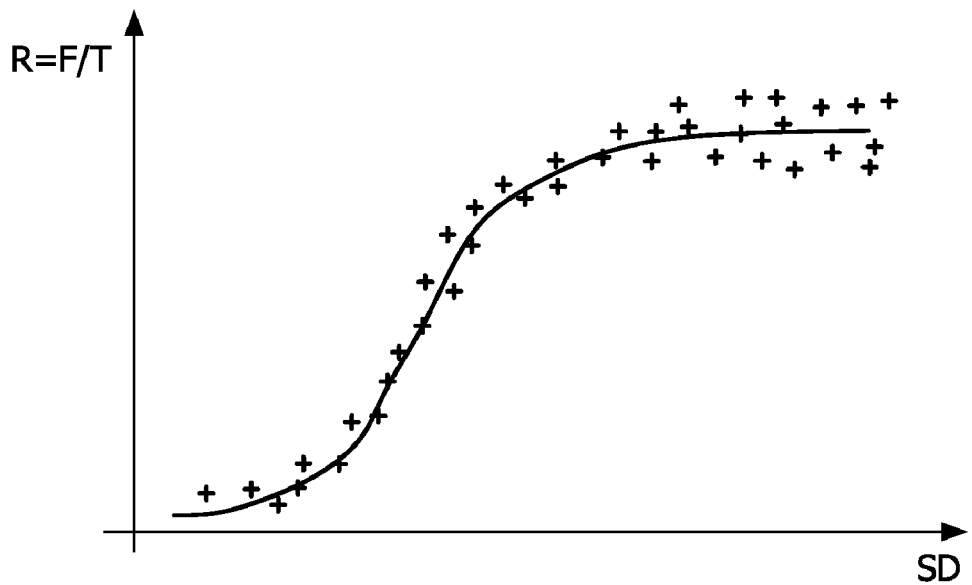
FIG. 3 is a diagram showing a ratio of fluorescence intensity to transmission intensity plotted as a function of a source detector distance as measured and calculated by the device of FIG. 1 for a first concentration of fluorescent contrast agent.
Figure 4:
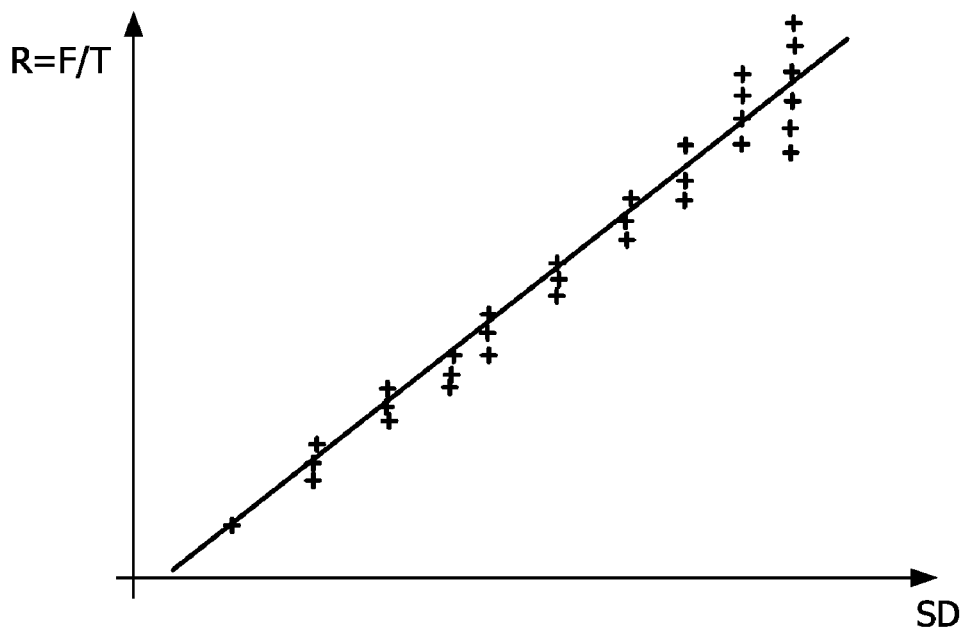
FIG. 4 is a diagram showing a ratio of fluorescence intensity to transmission intensity plotted as a function of a source detector distance as measured and calculated by the device of FIG. 1 for a second concentration of fluorescent contrast agent.

FIGS. 3 and 4 schematically show a diagram showing a ratio of fluorescence intensity to transmission intensity plotted as a function of a source detector distance as measured and calculated by the device of FIG. 1 for a first/second concentration of fluorescent contrast agent, respectively. In FIG. 3 and FIG. 4 said ratio R=F/T is plotted versus source detector distance, which is denoted SD.

FIG. 3 shows the case in which the fluorescence intensity data shows a non-linear behaviour due to self-absorption of the emitted fluorescence intensity by the contrast agent. This behaviour occurs in a high concentration regime, wherein certain structures of object 2 which contain higher concentrations of the contrast agent than surrounding parts of the object, e.g. tumours in human tissue such as female breast tissue, would appear as dark spots compared to a background intensity. According to FIG. 3, this type of undesired behaviour can be characterised by means of a roughly S-shaped curve when plotting R over SD.

FIG. 4 shows another plot of R vs. SD for a case of essentially optimum contrast agent concentration for achieving images, wherein a lesion in object 2, e.g. a tumour in human tissue, would appear as a bright spot compared to the background. This regime is characterised by an essentially linear behaviour of function R(SD).

By plotting the ratio R vs. source detector distance SD, as shown in FIGS. 3 and 4, on display means 14 (FIG. 1) a user of the inventive optical imaging system 1 may decide in real time whether or not concentration of the fluorescent contrast agent within object 2 is acceptable for a desired operation of the optical imaging system 1, e.g. for providing accurate images of potentially cancerous female breast tissue. However, as will be appreciated by a person skilled in the art, the present invention is not limited to this particular usage.

Alternatively or additionally, yet another module 10.1, 10.2, . . . of evaluating means 10 can be adapted to notify a first type of contrast agent concentration regime if ratio R varies linearly with distance (cf. FIG. 4). Accordingly, said module may further be adapted to notify a second type of contrast agent concentration regime, if said ratio varies non-linearly with distance. Said notifications, e.g. in the form of suitable control signals (not shown) may then be used by control unit 9 to control operation of the inventive optical imaging system 1. For instance, in the case depicted in FIG. 3, said control signal may be used to pause operation of the inventive system 1 until an optimum time point for imaging operation has been reached. As will be appreciated by a person skilled in the art, further concentration measurements by means of the method in accordance with the present invention may continuously be carried out to determine said optimum time point for imaging. In the same way, the method in accordance with the present invention may be used for measuring contrast agent kinetics. In this way, the method may further be used to determine an optimum injection dose of contrast agent into the object to be imaged.

Note that the above-described method in accordance with the present invention works directly on raw data provided by detector unit 6, such that no time and resource-consuming image reconstruction is required which further acts in favour of the real time capability of the proposed system and method.

As will further be appreciated by a person skilled in the art, the method in accordance with the present invention is able to give absolute concentration values of the contrast agent by determining the slope of the curve in FIG. 4 when calibrated by a set of measurements. A further one of said modules 10.1, 10.2, . . . may be implemented for this purpose.

In one embodiment of the present invention, plots as shown in exemplary fashion in appended FIGS. 3 and 4 are displayed to a user or operator through display means 14, so that the user or operator may react to control the system 1 by providing suitable input via input means 15, e.g. a keyboard or the like.

Alternatively or additionally, by means of yet another one of said modules 10.1, 10.2, . . . in evaluating means 10, a linear regression algorithm may be performed on the distance-dependent data provided by detector unit 6 in connection with certain predetermined thresholds in order to decide as to a linear or non-linear shape of the curve according to FIGS. 3 and 4. Again, if the ratio R=F/T shows linear behaviour as a function of source detector distance SD, then a control signal may be emitted, and control unit 9, i.e. evaluating means 10, accordingly commands laser controller 11, shutter controller 12 and motor controller 13 to perform irradiation of object 2 for acquiring optical images, as previously described. In contrast to this, if said ratio R behaves in a non-linear fashion as a function of source detector distance SD, then operation of the optical imaging system 1 is halted—with the exception of repetitive concentration measurements—until an optimum time point for imaging said object is reached.

Note that the above-described (software) modules 10.1, 10.2, . . . may be implemented in an existing optical imaging system having a suitable control unit, e.g. control unit 9, thus upgrading the system with respect to performing to method in accordance with the present invention.

Figure 5:
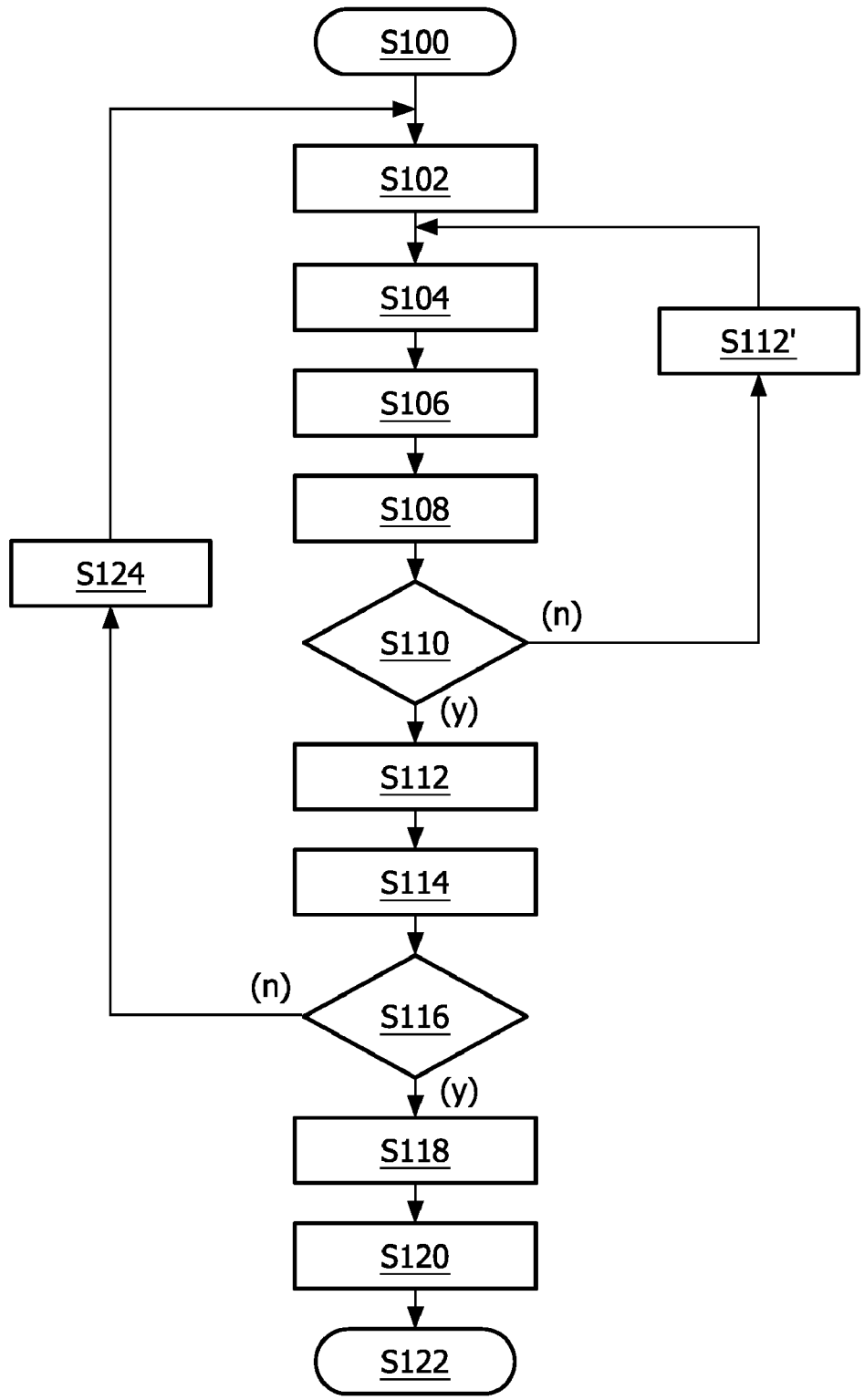
FIG. 5 is a flow chart of an embodiment of the method in accordance with the present invention.

FIG. 5 shows a flow chart of an embodiment of the method in accordance with the present invention. The method starts with step S100. In subsequent step S102 a counter variable, i, used in multiplexing said irradiating fibres 5.1, 5.2, . . . , 5.n wherein n denotes the total number of fibres, is set to an initial value, i.e. i=1.

Then, in subsequent step S104 an irradiating fibre corresponding to a current value of i is activated as previously described for irradiating an object comprising a fluorescence contrast agent. In subsequent step S106 distance-dependent transmission intensity data is gathered by the n detecting means provided by radiation guiding means 7 in connection with detector unit 6. Then, in subsequent step S108, filter means 8 are employed in order to gather fluorescence intensity data, as previously described.

In a following step S110 it is decided whether or not variable i has already reached its maximum value n. If the question in step S110 is answered in the affirmative (y), then in subsequent step S112 the ratio R=F/T is calculated as a function of source detector distance from the totality of raw data provided to evaluating means 10 by detector unit 6. If the question in step S110 is answered in the negative (n), then in a subsequent step S112' variable i is incremented (i=i+1), and method steps S104-S110 are repeated, as previously described.

Having calculated said ratio R in step S112, the method continues with step S114 wherein the behaviour of said ratio R as a function of source detector distance is analysed in order to determine a type of behaviour of said ratio R with source detector distance. As previously described, this can either be achieved by displaying a plot of said ratio R vs. source detector distance SD on a display means for visual inspection by an operator or by performing a mathematical regression on the data in order to determine its (non-)linearity.

If the question in subsequent step S116 is answered in the affirmative (y), i.e. said ratio shows linear behaviour with distance, then in subsequent step S118 operation of the optical imaging system in accordance with the present invention is started in order to acquire fluorescence imaging data of said object, in particular female breast tissue, for outputting to said display means or any other suitable output medium, e.g. a (magneto-)optical data carrier, in subsequent step S120.

The method in accordance with the present invention then terminates with step S122.

If the question in step S116 is answered in the negative (n) the method in accordance with the present invention is restarted beginning with step S102, preferably after waiting for a certain amount of time in step S124 in order to allow for a decrease of a contrast agent concentration which presumably is too high for optimum imaging operation (answer (n) in step S116, i.e. non-linear behaviour of ratio R as a function of source detector distance SD).

The invention claimed is:

1. A device comprising:
    a radiation source configured to produce electromagnetic radiation for irradiating a turbid medium at an excitation wavelength;
    a plurality of fluorescent electromagnetic radiation detectors configured to detect fluorescent electromagnetic radiation emitted at a fluorescence wavelength by a contrast agent applied to the turbid medium and in response thereto to produce fluorescence intensity data;
    a plurality of transmission electromagnetic radiation detectors configured to detect transmission electromagnetic radiation transmitted through the turbid medium at the excitation wavelength and in response thereto to produce transmission intensity data; and a processor, wherein distances between the fluorescent electromagnetic radiation detectors and the radiation source vary so as to produce distance-dependent fluorescence intensity data, and distances between the transmission electromagnetic radiation detectors and the radiation source vary so as to produce distance-dependent transmission intensity data, wherein the processor is configured to calculate ratios between the distance-dependent fluorescence intensity data and the distance-dependent transmission intensity data at a plurality of the distances, and to determine an amount of self-absorption of radiation by the contrast agent from a behavior of the ratios as a function of the distances.

2. The device of claim 1, further comprising a display for displaying a curve of said ratios plotted as a function of said distances.

3. The device of claim 1, wherein the fluorescent electromagnetic radiation detectors and the transmission electromagnetic radiation detectors are located at various positions relative to the turbid medium, and wherein the processor is configured to account for the relative positions of the fluorescent electromagnetic radiation detectors and transmission electromagnetic radiation detectors with respect to the turbid medium to determine which fluorescence intensity data and which transmission intensity data are to be included in the ratios, depending on said relative positions.

4. The device of claim 1, wherein the processor is configured to indicate a first type of concentration-related quantity of the contrast agent when the ratios vary linearly with said distance, and to indicate a second type of concentration-related quantity of the contrast agent when the ratios vary non-linearly with said distances.

5. The device of claim 1, wherein the fluorescent electromagnetic radiation detectors and transmission electromagnetic radiation are adapted to continuously produce said intensity data over a predetermined time interval.

6. The device of claim 1, further comprising:
a hollow unit for surrounding the turbid medium, said hollow unit comprising a plurality of first optical fibers in connection with said radiation source for irradiating the turbid medium inside said hollow unit, said hollow unit further comprising a plurality of second optical fibers in connection with the fluorescent electromagnetic radiation detectors and transmission electromagnetic radiation detectors for detecting radiation from the turbid medium inside said hollow unit.

7. The device of claim 6, wherein said first and second optical fibers are each distributed in essentially uniform fashion on a surface of said hollow unit.

8. The device of claim 6, comprising a multiplexer configured to selectively irradiate the turbid medium through one of said first optical fibers.

9. The device of claim 1, wherein the fluorescent electromagnetic radiation detectors are also the transmission electromagnetic radiation detectors.

10. The device of claim 6, wherein the fluorescent electromagnetic radiation detectors are also the transmission electromagnetic radiation detectors.

11. The device of claim 10, further comprising a switchable wavelength-selective filter provided in connection with one of: the second optical fibers; and the transmission electromagnetic radiation detectors.

12. The device of claim 9, wherein operation of the device is controlled in accordance with the concentration-related quantity of the contrast agent as determined by said device.

13. The device of claim 1, wherein the processor is further configured to determine a concentration-related quantity of the contrast agent from a slope of a linear relationship between the ratios and the distances.

14. A non-transitory computer program product, comprising:
first code sequences for receiving distance-dependent fluorescence intensity data descriptive of fluorescent electromagnetic radiation emitted by a turbid medium as measured at various distances between a radiation source that irradiates the turbid medium with transmission electromagnetic radiation, and various fluorescent electromagnetic radiation detectors configured to detect the fluorescent electromagnetic radiation;

second code sequences for receiving distance-dependent transmission intensity data descriptive of the transmission electromagnetic radiation transmitted through the turbid medium as measured at various distances between the radiation source and various transmission electromagnetic radiation detectors configured to detect the transmission electromagnetic radiation;

third code sequences for calculating ratios between the distance-dependent fluorescence intensity data and the distance-dependent transmission intensity data at a plurality of the distances, and to determine an amount of self-absorption of radiation by the contrast agent from a behavior of the ratios as a function of the distances.

15. A method, comprising:
employing a radiation source to irradiate a turbid medium with transmission electromagnetic radiation at an excitation wavelength;

detecting fluorescent electromagnetic radiation emitted at a fluorescence wavelength by a contrast agent applied to the turbid medium, the fluorescent electromagnetic radiation being detected at various distances between the radiation source and various fluorescent electromagnetic radiation detectors configured to detect the fluorescent electromagnetic radiation so as to produce distance-dependent fluorescence intensity data detecting transmission electromagnetic radiation transmitted at the excitation wavelength through the turbid medium at various distances between the radiation source and various transmission electromagnetic radiation detectors configured to detect the transmission electromagnetic radiation so as to produce distance-dependent transmission intensity data;

calculating ratios between the distance-dependent fluorescence intensity data and the distance-dependent transmission intensity data at a plurality of the distances; and determining a concentration-related quantity of the contrast agent from a behavior of the ratios as a function of the distances.

16. The method of claim 15, further comprising determining said concentration-related quantity continuously over a predetermined time interval.

17. The method of claim 15, further comprising outputting a control signal depending on a measure of said concentration-related quantity.

18. The method of claim 14, wherein the fluorescent electromagnetic radiation detectors are also the transmission electromagnetic radiation detectors.

* * * * *